United States Patent [19]

Brown et al.

[11] 4,347,312

[45] Aug. 31, 1982

[54] DETECTION OF ANTIBIOTICS IN MILK

[75] Inventors: Rodney J. Brown, Logan, Utah; Harold E. Swaisgood, Raleigh, N.C.

[73] Assignee: Research Triangle Institute, Research Triangle Park, N.C.

[21] Appl. No.: 131,914

[22] Filed: Mar. 20, 1980

[51] Int. Cl.$^3$ .................... G01N 33/54; C12N 9/96
[52] U.S. Cl. ........................ 435/7; 435/188; 435/810; 23/230 B; 424/12
[58] Field of Search .............. 435/7, 21, 28, 187, 435/188, 810; 424/8, 12, 85; 23/230 B; 426/665

[56] References Cited

U.S. PATENT DOCUMENTS

| | | | |
|---|---|---|---|
| 3,652,761 | 3/1972 | Weetall | 424/12 |
| 3,654,090 | 4/1972 | Schuurs et al. | 435/7 |
| 3,690,834 | 9/1972 | Goldstein et al. | 23/230 B |
| 3,766,162 | 10/1973 | Spector | 260/112 R |
| 3,817,837 | 6/1974 | Rubenstein et al. | 435/7 |
| 3,848,696 | 10/1974 | Wagner et al. | 260/404 |
| 3,850,752 | 11/1974 | Schuurs et al. | 435/7 |
| 3,878,187 | 4/1975 | Schneider et al. | 260/121 |
| 3,879,262 | 4/1975 | Schuurs et al. | 435/7 |
| 3,888,866 | 6/1975 | Leute et al. | 260/292 |
| 3,905,871 | 9/1975 | Rubenstein et al. | 435/7 |
| 3,951,748 | 4/1976 | Devlin | 435/7 |
| 4,039,652 | 8/1977 | Adams et al. | 424/1 |
| 4,069,105 | 5/1978 | Giaever | 23/230 B |
| 4,092,116 | 1/1978 | Singh | 424/12 |
| 4,107,157 | 8/1978 | Spector | 260/112 B |
| 4,133,639 | 1/1979 | Harte | 23/230 B |

OTHER PUBLICATIONS

Wal, "Radioimmunoassay for the Detection of Penicilloyl Groups in Biological Fluids after Therapy with Penicillin G.", Chem. Absts., vol. 86, No. 19, p. 4 (1977), abs. No. 133244e.

Schuurs et al, "Enzyme Immunoassay", Clin. Chem. Acta, vol. 81, No. 1, (1977) pp. 1-40.

Primary Examiner—Thomas G. Wiseman
Attorney, Agent, or Firm—Cushman, Darby & Cushman

[57] ABSTRACT

A method for detecting the presence of antibiotics in milk which comprises the steps of: (a) contacting a solid matrix having attached thereto a purified immobilized antibody with a volume of milk and an enzyme-labeled antibiotic, said antibody being specific to said antibiotic; (b) separating the matrix from the milk and rinsing the matrix with water to remove excess milk and enzyme-labeled antibiotic; (c) contacting the rinsed matrix with a substrate, said substrate in the presence of said enzyme-labeled antibiotic exhibiting a color change the amount of which is quantitatively related to the amount of enzyme-labeled antibiotic; and (d) measuring the amount of antibiotic present in said milk by comparing the color change in said substrate with a standard.

Also provided is a method for producing purified antibodies for use in the foregoing detection method by: (a) convalently conjugating an antibiotic having a lactam-ring in the molecule to a protein capable of binding thereto through said lactam-ring; (b) injecting into a host animal capable of raising antibodies specific to said antibiotic the conjugate obtained in step (a) so as to raise said specific antibodies; (c) covalently conjugating the same antibiotic in step (a) to a second protein capable of binding thereto through said lactam-ring and different than the protein used in step (a) to form a second conjugate; (d) covalently binding said second conjugate to a solid matrix to form an affinity matrix for purifying the antibodies; (e) isolating and purifying the specific antibodies raised in step (b) by contacting the host animal serum with the affinity matrix; and (f) recovering the specific antibodies in pure form.

14 Claims, 8 Drawing Figures

DETECTION OF ANTIBIOTICS IN MILK

BACKGROUND OF THE INVENTION

The present invention is directed to a relatively simple and inexpensive method for detecting the presence of antibiotics in milk.

Mastitis is probably the most frequently observed disease state of dairy cows. Treatment of mastitis in dairy cows usually is carried out by either injection or udder infusion of antibiotic preparations, most notably penicillin. An undesirable consequence is that small amounts of antibiotics are found in some milk obtained from treated animals when collected from the farm. Persistence of these antibiotics throughout processing causes failure of culture organisms and leaves residual antibiotics in consumer products. Allergic reactions to antibiotics and loss of sensitivity of the general population to antibiotics, caused by continual long term exposure to low doses, are realities which must be faced.

The presence of penicillin in the milk supply is thus a major concern because it constitutes a public health hazard. Also, such contaminated milk is not suitable for manufacture of cultured dairy products. Most fluid milk is now transported in bulk tank trucks so contaminated milk from a single cow can subsequently contaminate the milk from many herds in a large bulk tank truck. Thus, a rapid and simple test which could be performed by the hauler or farmer prior to loading the herd milk into the bulk tank truck could result in a great savings.

Present methods for detecting antibiotics generally require microbial assays and, hence, considerable time and laboratory facilities are necessary. Present chemical tests do not have sufficient sensitivity to detect the minimum tolerable levels of antibiotic concentration.

A radioimmunoassay technique which utilizes the competition between radio-labelled antibiotic and sample antibiotic for antibody would be very sensitive; however, this method would require trained personnel and expensive equipment.

Thus, there has not been available a fast, acceptable test for antibiotics which can be routinely used by farm or dairy plant workers. As noted, the limiting factors in the available tests have been sensitivity to the low levels of antibiotics which must be detected and the time required to conduct the tests. Where these two factors are overcome, expense of the test and equipment required become prohibitive, especially for on the farm use.

Accordingly, and as a primary object of the present invention, there is provided herein a test which overcomes the foregoing problems.

A further object of the present invention is to provide a test designed for detection or measurement of benzylpenicillin and other antibiotics which may be found in milk.

It is yet another object of our invention to provide a method for the detection of all forms of penicillin at very low concentrations in accordance with the following guidelines:

1. The test should be sensitive to 0.01 units/ml;
2. Time required for a single test should not exceed about 10 minutes;
3. Untrained personnel should be capable of performing the test. (The present test has been designed specifically for use at the farm by the farmers themselves and by milk truck drivers.);
4. The cost per test should be as inexpensive as possible.

With prior procedures, these objectives could not be attained since (a) required incubation times of the binding partners were excessively long; (b) expensive, specialized equipment was required; and (c) trained laboratory personnel were required to perform the test.

These and other objects of the invention will be more apparent from the discussion below.

SUMMARY OF THE INVENTION

The present invention provides a method for determining the quantity of antibiotics in milk by exposing a test sample of the milk and, simultaneously or successively, a solution containing an enzyme-labeled form of the antibiotic, to an immobilized antibody whereby competition for the binding sites will be a function of the relative concentrations of the labeled and unlabeled antibiotics. The concentration of the antibiotic in the milk sample can subsequently be determined by measuring the amount of bound enzyme-labeled antibiotic. The antibody may be covalently bound or adsorbed to a variety of surfaces in various geometrical configurations; for example, to the walls of polystyrene or glass test tubes, to the surface of porous beads, to the wells of microtiter plates, or to the surface of a rod used as a "dip stick."

Thus, the present method for detecting the presence of antibiotics in milk generally comprises the steps:
(a) contacting a solid matrix having attached thereto a purified immobilized antibody with a volume of milk and an enzyme-labeled antibiotic, said antibody being specific to said antibiotic;
(b) separating the matrix from the milk and rinsing the matrix with water to remove excess milk and enzyme-labeled antibiotic;
(c) contacting the rinsed matrix with a substrate, said substrate in the presence of said enzyme-labeled antibiotic exhibiting a color change the amount of which is quantitatively related to the amount of enzyme-labeled antibiotic; and
(d) measuring the amount of antibiotic present in said milk by comparing the color change in said substrate with a standard.

In addition, the present invention further provides for a means of preparing a purified antibody which is suitable for use in detecting the amount of antibiotic present in milk by:
(i) covalently conjugating an antibiotic having a lactam-ring in the molecule to a protein capable of binding thereto through said lactam-ring;
(ii) injecting into a host animal capable of raising antibodies specific to said antibiotic the conjugate obtained in step (i) so as to raise said specific antibodies;
(iii) covalently conjugating the same antibiotic as used in step (i) to a second protein capable of binding thereto through said lactam-ring and different than the protein used in step (i) to form a second conjugate;
(iv) covalently binding said second conjugate to a solid matrix to form an affinity matrix for purifying the antibodies;
(v) isolating and purifying the specific antibodies raised in step (ii) by contacting the host animal serum with the affinity matrix; and
(vi) recovering the specific antibodies in pure form.

As used herein, the term antibiotic refers to those antibiotics which contain a lactam-ring in the molecule. Inclusive of such antibiotics are the penicillins, such as benzylpenicillin, and cephalosporins.

The enzyme-labeled antibiotics (i.e., conjugate) employed must have a reactive site wherein the affinity for bonding sites are similar for both the free antibiotic and the enzyme-labeled antibiotic. The antibiotic is labeled with an enzyme, in a conventional manner, by covalently bonding the enzyme to the antibiotic through a carboxy group of the antibiotic. Horseradish peroxidase is preferred due to its stability, but other enzymes could be utilized such as alkaline phosphatase, which while not as stable, is more sensitive.

The term substrate as used herein refers to a material which undergoes a color change in the presence of the enzyme (i.e., enzyme-labeled antibiotic). The degree of color change is quantitative to the amount of enzyme present. The preferred substrate is a mixture of m-phenylenediamine and hydrogen peroxide.

In preparing the purified antibody, it is necessary to prepare two different protein conjugates with the antibiotic, one which is used to raise the needed antibodies and the other for separation and recovery of the desired specific antibody in a purified form by affinity chromatography. Suitable proteins are those capable of binding to the antibiotic through its lactam-ring. Exemplary proteins include gamma globulins and serum proteins.

Immobilization of the purified antibody may be carried out in a known manner, for example, by covalent binding to a solid matrix (e.g., glass beads, tubes, plates or cyanogen bromide activated agarose) or by adsorption (e.g., to polystyrene).

Instead of immobilizing the whole antisera or γ-globulin fraction as currently practiced in immunoassay procedures, the purified specific antibody used herein is obtained by affinity chromatography. As a consequence, the surface concentration of specific binding sites is much greater since it is not diluted by immobilization of non-specific antibodies or other contaminating proteins. Since the rate of reaction between binding partners depends upon the surface concentration of specific binding sites as well as upon the concentration of the binding partner in solution, the immobilization of purified specific antibody accomplishes the following results: (a) the length of required incubation time is greatly reduced, and (b) the amount of surface area required to contain a particular quantity of binding partners is greatly reduced negating the necessity for using a volume of porous support material.

The concentration of antibiotic in the sample is measured by the result of its competition with the enzyme-labeled antibiotic for the specific binding sites of the immobilized antibody. The reagent chosen as a substrate for the enzyme has a high reaction rate and the reaction catalyzed (i.e., oxidation of the substrate) produces a color change in the substrate. The substrate is stable in solution for long periods of time (e.g., up to a month) and can be added as a single reagent.

Summarizing the test method of the present invention:

1. A specified volume of milk is exposed to the purified specific immobilized (to the test surface) antibody for a specified short period of time; as, for example, by addition to a test tube, by addition to a microtiter well, or by immersion of a "dip stick" in the said volume.

2. A specified quantity of enzyme-labeled antibiotic is exposed for a specified short period of time to the purified specific immobilized antibody either together with, or in a step following exposure to, the sample.

3. Following a rinse procedure, a specified quantity of substrate solution is exposed to the test surface and the degree of color development is quantitated after a specified short period of time.

It should be noted that the use of one component in an insolubilized form and one covalently linked to an enzyme has been employed for determining components of an antigen-antibody reaction as described in U.S. Pat. Nos. 3,654,090 and 4,039,652. The present method has the distinct feature of using a much higher surface concentration of binding partner sites by utilizing an affinity-purified specific immobilized antibody. The present method further provides for a large decrease in the required incubation time and the amount of surface area necessary to provide a quantitative determination of low antibiotic concentrations (e.g., 0.001 units/ml) by using such concentrated immobilized sites due to the use of a purified antibody.

Furthermore, a unique substrate has been discovered which is a stable reagent and provides quantitative color change in the desired concentration measurement range.

DETAILED DISCUSSION OF THE INVENTION

For purposes of the discussion which follows, benzylpenicillin was used as the trial antibiotic, but the method is designed to be easily adapted for the detection or measurement of other antibiotics which contain a lactam ring within the antibiotic molecule.

PREPARATION OF PURIFIED SPECIFIC IMMOBILIZED ANTIBODY

Figure 1:
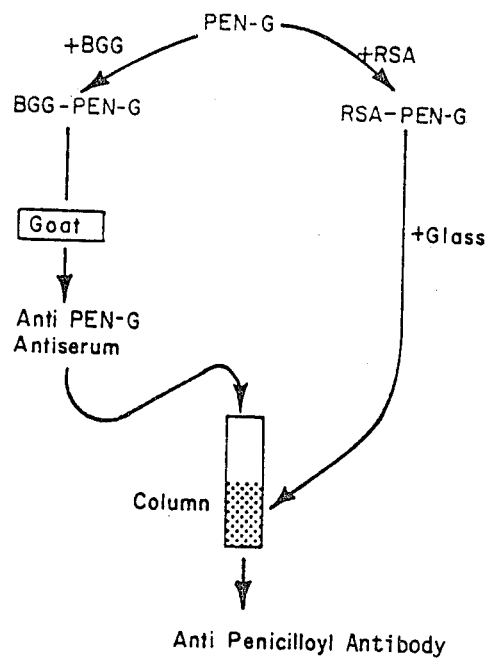
FIG. 1 schematically depicts preparation of the immobilized antibody.

The required immobilized antibody for detecting antibiotics in milk must be both specific and in a purified state. Benzylpenicillin is preferred as the resulting penicilloyl antigenic determinant which is reactive with all types of penicillin.

Benzylpenicillin (Penicillin-G) (PEN) was covalently conjugated to bovine gamma globulin (BGG) and to rabbit serum albumin (RSA) through the β-lactam ring of the penicillin molecule and the α-amino groups of lysine side chains on the proteins. This ensures that there is only one link from each penicillin molecule to the protein and that all of the conjugates are the same. The reactions are among those which have been proposed as possible mechanisms for conjugation of β-lactam antibiotics to proteins in vivo, giving rise to allergies to these antibiotics. Although each penicillin molecule is bound by only one link to a protein molecule, each protein molecule carries many such links to individual penicillin molecules.

In order to raise antibodies to penicillin, the PEN-BGG conjugate was suitably prepared, then injections into a goat's skin were made at ten day intervals. Serum was collected and held at −10° C. until needed. The serum produced a positive ring test for antibody against RSA conjugated PEN, indicating presence of antipenicilloyl antibody (Ab). Preparation of antibody with the penicilloyl as the antigenic determinant allows all types of penicillin to bind to the antibody.

RSA-PEN conjugates were bound convalently to porous glass beads having a reactive surface suitable for covalent bonding to the conjugate by contacting the conjugates with the beads at a pH ranging from about 5 to 8.

PURIFICATION OF ANTIBODY AND PREPARATION OF AFFINITY MATRIX

Glass beads having a suitable surface for bonding the conjugate may be prepared by:
 a. silanizing and succinylating the glass beads to provide a succinamidopropyl-surface;
 b. converting the succinamidopropyl-surface to the acyl chloride derivative by treatment under anhydrous conditions.
 c. reacting the acyl chloride derivative with either 3-mercaptopropinic acid or mercaptoacetic acid under anhydrous conditions whereby the surface of the glass beads is activated; and
 d. drying the activated glass beads.

The silanizing and succinylating is carried out according to known procedures. Thus, silanizing is accomplished generally by treating the inorganic metal oxide material with an aqueous solution (e.g., about 10%) of the triethoxyaminopropylsilane at a pH of about 4. Thereafter, succinylating is accomplished by treating the material with either an aqueous solution of succinic anhydride at a pH of about 6, or an aqueous solution of succinic acid and carbodiimide.

Formation of the acyl derivative is accomplished by reaction with thionyl chloride dissolved in an inert organic solvent (e.g., methylene chloride) in the absence of water, i.e., under anhydrous conditions.

At this point, the acyl derivative is reacted with either mercaptopropionic acid or mercaptoacetic acid dissolved in an inert organic solvent such as methylene chloride in the absence of water. Upon completion of the reaction, the material is dried, in vacuo, and stored until ready for use.

Immobilization of the RSA-PEN conjugate is accomplished by simply adding a solution of the conjugate at a pH around neutrality (e.g., 5 to 8) to a solid matrix (e.g., dry glass beads). Hence, the procedure is simple and mild.

The antiserum was then purified by passing through columns of these beads and the columns thoroughly washed with physiologically buffered saline solution (PBS) then eluted with 0.1 M acetic acid. The eluent was mixed immediately with pH 10, 0.1 M sodium bicarbonate to neutralize the acid.

Everything discussed to this point is summarized in FIG. 1. Various gels were compared with glass beads and found to be less satisfactory. Non-conjugated penicillin-G and 6-aminopenicillenic acid were tried in place of RSA-PEN on the glass and also proved inferior for elution of the purified antibody.

The test we have developed is similar to a radioimmunoassay, but uses an enzyme as the label instead of a radioactive marker. Enzyme immunoassay is a relatively new procedure, but enough information has been collected to indicate that for the present method horseradish peroxidase (HRP) is the enzyme of choice. It is very stable under favorable storage conditions, and provides for a wide choice of substrates to choose between.

The preferred substrate is m-phenylenediamine, which, unlike other substrates tested, is stable in the presence of the co-substrate, hydrogen peroxide. The rate constants for the reactions are $9 \times 10^8$ $M^{-1}sec^{-1}$ for the $H_2O_2$ and $10^6$ $M^{-1}sec^{-1}$ for m-phenylenediamine. Though two substrates with rate constants slightly faster than this were tested, the stability, solubility in aqueous solutions, and large visible color change upon reaction render this reagent preferred. The substrate mixture used is 2.8 mM $H_2O_2$ and 1.4 mM m-phenylenediamine. This mixture is stable for over a month.

SUBSTRATE STABILITY

Among the substrate mixtures tested, m-phenylenediamine was the most stable when mixed with the co-substrate hydrogen peroxide. Stabilities of at least one month were observed. After this period a rust color begins to develop, making it unsuitable as a reagent.

Other substrates which were found either unstable or insoluble in the presence of hydrogen peroxide and thus unsuitable included -guaicol, 5-aminosalicylic, o-phenylenediamine, p-phenylenediamine; aniline, 4-aminosalicylic acid and ortho-dianisidine.

The advantageous characteristics of m-phenylenediamine include:
 1. Very soluble in water;
 2. Stable in the presence of peroxide;
 3. Distinct color change in visible range upon reaction; and
 4. Developed color is stable.

The substrate meta-phenylenediamine, when mixed with peroxide (second substrate) is stable over long time (one month) whereas other peroxidase substrates oxidize (color) even when peroxidase is not present.

PREPARATION OF ENZYME LABELED ANTIBIOTIC

PEN was linked to HRP by the method used for BGG and RSA as shown earlier and also by an amide linkage using a carbodiimide carboxylactivating reagent. This second method was most satisfactory. Since the penicilloyl group is not formed, the conjugate is more like free penicillin in its binding properties to the antibody. The activity of the PEN linked HRP is greater than 90% that of the free enzyme. As with BGG and RSA, there are many PEN molecules bound to each enzyme molecule.

Figure 2:
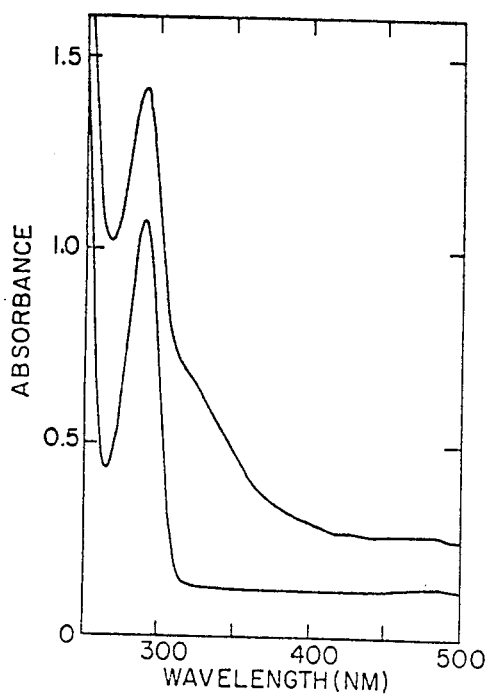
FIGS. 2 and 3 are absorbance spectra of substrate mixtures.
Figure 3:
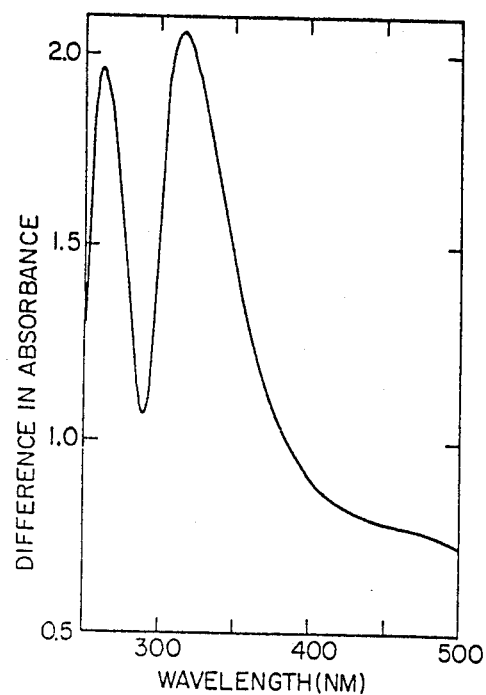

FIG. 2 shows the absorbance spectra of the substrate mixture both before (lower curve) and after (top curve) reaction with the HRP-PEN conjugate. The substrate mixture was diluted 1/20 in order to allow spectrophotometer readings to be made. The undiluted sample turns from clear to a dark rust color, which far exceeds the range of the spectrophotometer. FIG. 3 is a difference spectra showing that the largest change in absorbance is at 315 nm with another peak at ca. 260 nm. This plot was made with the substrate diluted 1/5.

Figure 4:
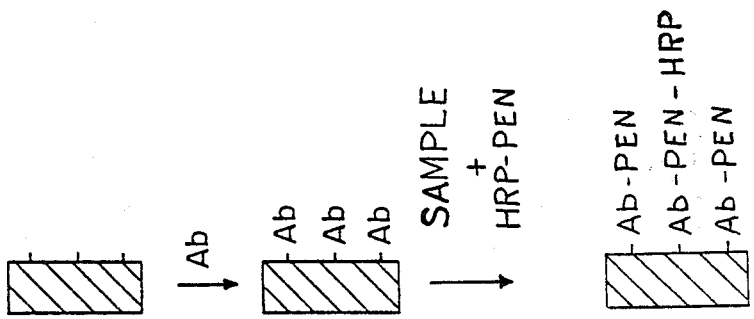
FIG. 4 is a schematic depiction of the assay procedure.

In practice, then, one has the simple assay procedure shown schematically in FIG. 4 and outlined below. The antibody-coated assay tubes are prepared beforehand by allowing the antibody solution to stand in the tubes for 12 hours after which they are water-rinsed. They should not be permitted to dry before being used.

GENERAL ASSAY PROCEDURE

1. Introduce the milk sample plus HRP-PEN (enzyme labeled antibiotic) solution to antibody coated tube. Wait five minutes.
2. Empty tubes and rinse twice with Tween 20 (0.05%).
3. Introduce substrate mixture. Wait 1–3 minutes for a color change.
4. Measure $A_{330}$ or visually compare with color chart.

The purified specific immobilized antibody is attached to a solid matrix such as the inside of a polystyrene or glass test tube, beads in a column, a rod to be used as a "dip stick" or in a variety of other configurations depending on the application desired. For very efficient use with an average reading time of less than one minute per sample, the insides of the wells in microtiter plates may be used as the matrix. A solution of HRP-PEN conjugate (i.e., the enzyme-labeled antibiotic) is mixed with the sample being tested and exposed to the immobilized antibody. Penicillin in the sample competes with HRP-PEN for and antibody binding sites. Therefore, the amount of HRP-PEN bound depends on the PEN concentration in the milk sample. After a few minutes, the bound antibody is vigorously rinsed with a 0.05% Tween-20 detergent solution. The amount of enzyme bound is very sensitively determined by exposing the rinsed antibody to the substrates for HRP.

Figure 5:
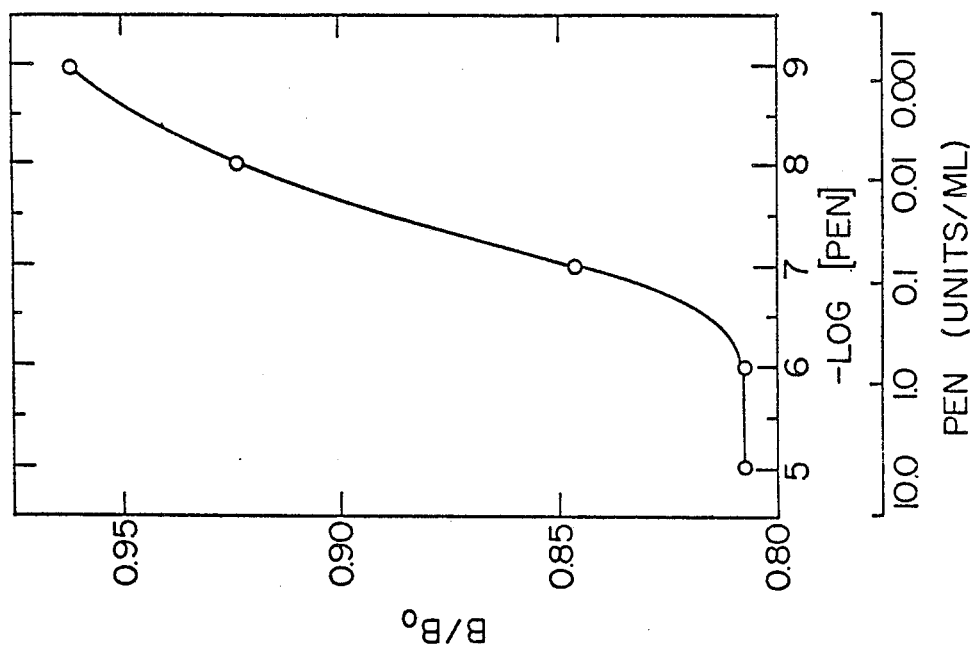
FIGS. 5 and 6 are graphs of an assay result using a spectrophotometer.

The measurement of the enzyme reaction can be either visual or with a spectrophotometer. FIG. 5 shows the results of an assay using the spectrophotometer and with the antibody bound on the insides of polystyrene tubes. $B/B_o$ represents measured absorbance divided by the absorbance of the sample with no PEN present.

Figure 6:
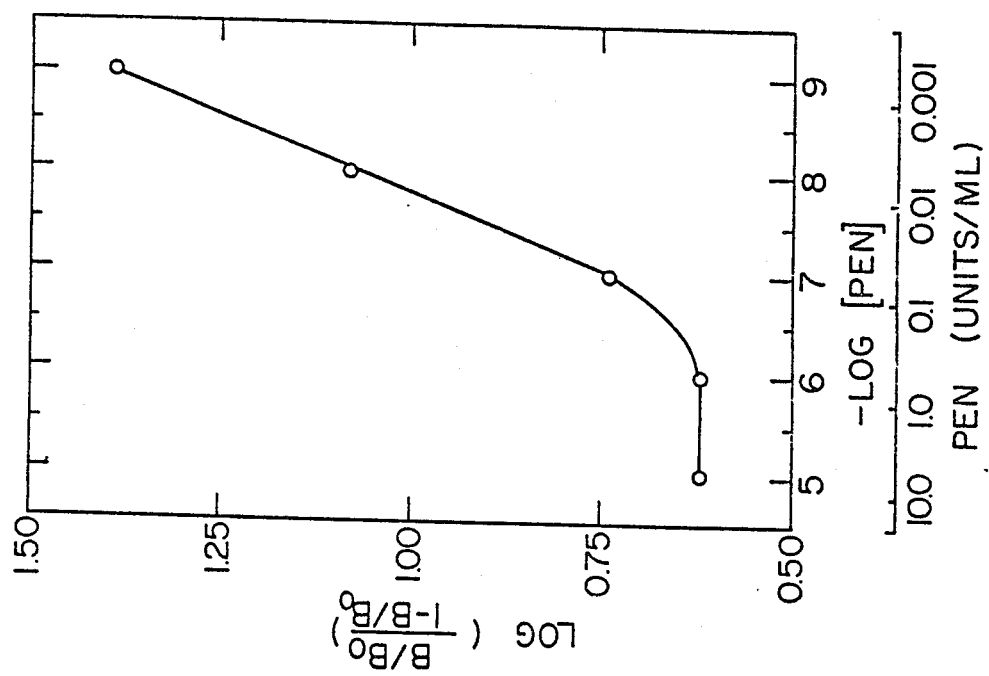

The same data is plotted in FIG. 6 in a way which makes it easier to use. This allows quantitative measurement by comparing with a standard curve. Variation in the ratios of sample size to amount of antibody used or to amount of HRP-PEN conjugate allows the sensitivity to be adjusted over a very large range.

Figure 7:
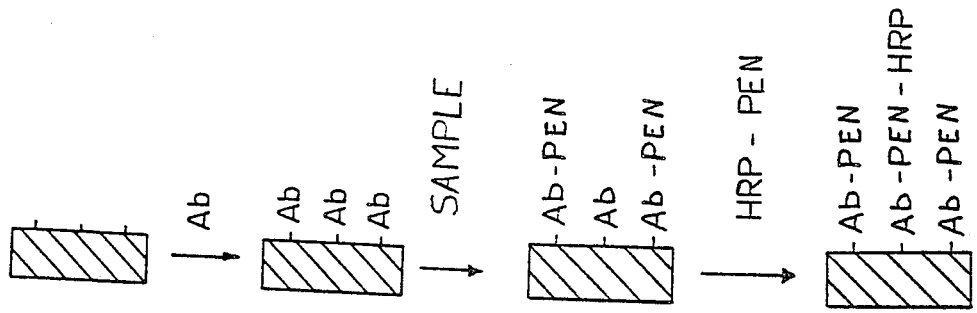
FIGS. 7 and 8 illustrate alternative assay procedures.

We have also found that separating the sample and HRP-PEN steps as shown in FIG. 7 give results equivalent to those in FIGS. 5 and 6. The time of the assay is slightly increased though, by the two separate binding steps.

This alternative assay procedure consists of the following steps:
1. Introduce sample into antibody-coated tube. Wait five minutes.
2. Empty and rinse twice with water.
3. Introduce HPR-PEN solution to tube. Wait five minutes.
4. Empty and rinse twice with Tween 20 (0.05%).
5. Introduce substrate mixture to tube.
6. Measure $A_{330}$ or visually compare with color chart.

Figure 8:
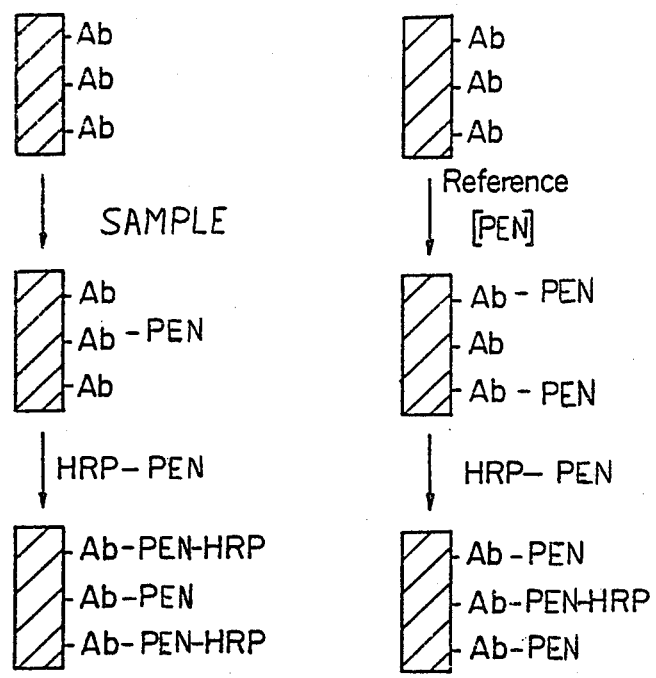

FIG. 8 illustrates the test as it would be used to detect a set cut-off level of penicillin in a sample of milk or other fluid. Two samples are run side by side, one the milk sample being tested and the other a standard solution from the linear portion of the curve in FIG. 6. The right column of FIG. 8 represents the standard or reference solution with the other two columns representing samples of lower or higher penicillin concentration. When prepared as a "test kit" ready for use, the test is very simple and easy to understand and use.

A further alternative assay procedure consists of the following:
1. Introduce milk sample into one antibody-coated tube and standard PEN solution into a second. Wait five minutes.
2. Empty tubes and rinse twice with water.
3. Introduce HRP-PEN solution to both tubes. Wait five minutes.
4. Empty tubes and rinse twice with Tween 20 (0.05%).
5. Introduce substrate mixture to both tubes. Wait 1–3 minutes.
6. Compare color developed.

The cost of the test depends on several factors, but is basically very low. The material costs are for the matrix to which the antibody is bound, the antibody itself, the enzyme and the enzyme substrate plus some pure penicillin for conjugation to the enzyme. The matrix can vary from a polystyrene test tube at ca. 3 cents each or a well in a microtiter plate to slightly more expensive arrangements. The enzyme and substrate have been chosen to be very inexpensive and the amounts used are low. The antibody is possibly the most expensive ingredient, but the amount used for a test is so low that is also becomes almost negligible. For example, using polystyrene tubes as the matrix, a solution of antibody at a concentration of 0.1 mg per ml was used repeatedly to coat tubes with no detectable decrease in the concentration of the stock solution. Removal of bound PEN and HRP-PEN is also possible for reuse of the same matrix but the savings is probably not worth the risk of decreasing the precision of the test by poor rinsing, etc. The combination of these parts to make a test for a chosen application can change the cost slightly, mostly due to the matrix. Interestingly, as the test becomes more sensitive, the amount of antibody and other things (and therefore the cost of the test) are decreased.

PREPARATION OF CONJUGATES 1.6 g of bovine gamma globulin was placed in a minimum volume sodium carbonate buffer at a pH of 10.4 and temperature of 4° C., to which 2.0 g of penicillin-G (PEN) was added and the pH adjusted to 9.6. After 16 hours, an additional 0.75 g PEN was added, the temperature being maintained at 4° C. Eight hours later, another 0.75 g PEN was added. Twelve hours later the mixture was eluted through a Sephadex G-200 column. After elution, cysteine hydrochloride was added to give a concentration of 0.1 molar and the pH was adjusted to 7.5. The mixture was then incubated at 37° C. for 1 hour. Thereafter, the mixture was again eluted through a Sephadex G-200 column, washed with water and the resulting PEN-BGG conjugate lyophilized for storage until ready for further use.

In order to raise antibodies the PEN-BGG conjugate was suitably prepared for injection into the host animal, a goat. 3.5 mg of the lyophilized PEN-BGG was solubilized in 2 ml of a physiological buffer to which was then added 3 ml of complete Freund's Adjuvant to provide the desired emulsion for injection. 3 ml of the emulsion (equivalent to 2 mg PEN-BGG) was injected into the skin of a goat. The 3 ml injection was repeated twice again, with a period of ten days between each injection. Ten days after the third and final injection, blood was collected from the goat and the specific purified antibody (Ab) separated by affinity chromatography using glass beads according to the procedure outlined above.

The foregoing procedure used to prepare the PEN-BGG conjugate was repeated except that rabbit serum albumin was substituted for bovine gamma globulin. The RSA-PEN conjugate so obtained was covalently bonded to the glass beads used to separate the specific purified antibody.

From the foregoing it is clear that an essential feature of the present method is the use of a purified specific immobilized antibody. This feature allows the desired sensitivity to be achieved with greatly reduced surface area for immobilization of the antibody. The antibody is purified in a single step by an affinity chromatography procedure. Using such a purified antibody thereby enables one to obtain the same sensitivity with far less total protein. Consequently, these results a greater concentration of specific binding sites since there is no dilution by immobilization of non-specific antibodies or other contaminating protein. This permits fewer non-specific interactions, and due to the higher concentration of immobilized binding sites, it reduces the time required for binding. In immunoassay procedures currently practiced, one will find that the incubation times range anywhere from about ½ hr. to 26 hrs., usually much greater than ½ hr.

A second essential feature of the present method is the manner in which the HRP-PEN (horseradish peroxidase-penicillin conjugate) is labeled. The antibody is actually directed to a penicilloyl derivative because the antibody is immobilized through a lactam ring to make the antibody. However, in labelling the penicillin with horseradish peroxidase-the enzyme is reacted with a carboxy group rather than the lactam ring used to prepare the antibody. Therefore, the HRP-PEN prepared in this manner has less affinity for the antibody than would have been the case if HRP-PEN was prepared by reaction with the lactam ring. In other words, using this procedure, the free penicillin will compete more efficiently and effectively with HRP-PEN for the antibody binding sites. Thus, the HRP-PEN behaves more like free penicillin with respect to its binding to the antibody.

Such a procedure avoids preparation of a conjugate of the penicillin in the same manner used to make the purified antibody, and uses the simplest method for making the antibody and for labeling the penicillin. It is important that the competing molecule have about the same binding affinity for the antibody as free penicillin. The m-phenylenediamine is the preferred substrate for peroxidase because of its stability in the presence of hydrogen peroxide. As a result, one can prepare this substrate solution as one solution, and thus eliminate the number of manipulations that a tester would have to go through in using the test.

The invention having been thus described, it will be apparent to those skilled in the art that variations may be employed without departing from the scope of the present invention which may comprise, consist or consist essentially of the herein recited materials and steps.

What is claimed is:

1. A method for detecting the presence of antibiotics having a lactam ring in milk which comprises the steps of:
   (a) contacting a solid matrix having attached thereto a purified immobilized antibody with a volume of milk and an enzyme-labeled antibiotic having a lactam ring, said antibody being specific to said antibiotic and said enzyme-labeled antibiotic being covalently conjugated to the antibiotic through a carboxy group in the antibiotic molecule;
   (b) separating the matrix from the milk and rinsing the matrix with water to remove excess milk and enzyme-labeled antibiotic;
   (c) contacting the rinsed matrix with a substrate, said substrate in the presence of said enzyme-labeled antibiotic exhibiting a color change the amount of which is quantitatively related to the amount of enzyme-labeled antibiotic; and
   (d) measuring the amount of antibiotic present in said milk by comparing the color change in said substrate with a standard, said purified immobilized antibody having been prepared according to the steps which comprise:
      (i) covalently conjugating an antibiotic having a lactam-ring to a protein through said lactam-ring;
      (ii) injecting into a host animal capable of raising antibodies specific to said antibiotic the conjugate obtained in step (i) so as to raise said specific antibodies;
      (iii) covalently conjugating the sme antibiotic as used in step (i) to a second protein capable of binding thereto through said lactam-ring and different than the protein used in step (i) to form a second conjugate;
      (iv) covalently binding said second conjugate to a solid matrix to form an affinity matrix for purifying the antibodies;
      (v) isolating and purifying the specific antibiodies raised in step (ii) by contacting the host animal serum with the affinity matrix; and
      (vi) recovering the specific antibodies in a pure form and immobilizing the purified antibodies on a solid matrix.

2. The method of claim 1 wherein said solid matrix is selected from the group consisting of the inside of a polystyrene or glass test tube, beads in a column and a rod.

3. The method of claim 1 wherein said substrate is a mixture of m-phenylenediamine and hydrogen peroxide.

4. The method of claim 3 wherein the measuring is done visually.

5. The method of claim 3 wherein the measuring is done on a spectrophotometer.

6. The method of claim 1 wherein said immobilized antibody and enzyme-labeled antibiotic are simultaneously contacted with said volume of milk.

7. The method of claim 1 wherein step (a) further comprises successively:
   (i) first contacting said volume of milk with the matrix;
   (ii) rinsing said matrix to remove the milk;
   (iii) contacting the rinsed matrix with said enzyme-labeled antibiotic; the period of contact in (i) and (iii) being equal.

8. The method of claim 1 wherein said purified immobilized antibody is attached to said matrix by adsorption.

9. The method of claim 8 wherein said matrix is polystyrene.

10. The method of claim 1 wherein said purified immobilized antibody is attached to said matrix by covalent bonding.

11. The method of claim 1 wherein said enzyme-labeled antibiotic is horseradish peroxidase which is covalently conjugated to benzylpenicillin.

12. The method of claim 1 wherein said purified immobilized antibody is characterized by penicilloyl as the antigenic determinant.

13. The method of claim 1 wherein said antibiotic is benzylpenicillin, the protein in step (i) is bovine gamma globulin, said second protein is rabbit serum albumin and the host animal is a goat.

14. The method of claim 1 wherein the solid matrix of step (iv) is glass.

* * * * *